US00PP34882P2

(12) United States Plant Patent
Bourne

(10) Patent No.: US PP34,882 P2
(45) Date of Patent: Jan. 3, 2023

(54) GRAPEVINE NAMED 'SV35-182-213'

(50) Latin Name: ***Vitis vinifera* L.**
Varietal Denomination: SV35-182-213

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 17/803,363

(22) Filed: May 27, 2022

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./156, 205, 207
See application file for complete search history.

*Primary Examiner* — Karen M Redden
(74) *Attorney, Agent, or Firm* — Eric C. Cole; Baker Manock & Jensen, PC

(57) ABSTRACT

A new and distinct variety of grapevine plant named 'SV35-182-213' particularly characterized by its large, crisp, sweet berries with muscat flavor. The natural cluster size is medium, eliminating the need to hand trim the clusters. The vines are very responsive to exogenous gibberellic acid application and trunk girdling and produce berries which are about 30% larger than natural size. Vines are fruitful when spur pruned to two buds per cane with new shoots producing one or two clusters per shoot.

4 Drawing Sheets

Scientific name of the genus and species of the plant claimed: The plant claimed relates to a new and distinct variety of *Vitis vinifera* L.

Variety denomination:

The plant claimed shall be known as 'SV35-182-213'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV35-182-213'. As used herein, 'grapevine' refers to all plant parts including vines, shoots, canes, tendrils, leaves, fruit and roots of 'SV35-182-213'. Grapevine named 'SV35-182-213' is the result of an effort to produce a crisp, sweet seedless table grape with muscat flavor. This new grapevine variety originated from a cross conducted in May 2014 near McFarland, Calif. between female parent grapevine named 'SV21-66-226' (U.S. Plant Pat. No. 24,531) and male parent grapevine named 'SV27-82-371' (unpatented). Resultant ovules from the cross were harvested 42 days after pollination and cultured on McCown's Wood Plant Medium. Subsequently, the resultant embryonic plants were extracted from those ovules and were cultured in the same medium in the laboratory under twelve hours of light from standard fluorescent lamps at 27 C. The seedlings from this effort were transplanted to the greenhouse in November of 2014 and grown at 27 C with 12 hours illumination under high pressure sodium vapor lamps. The seedling population of 75 seedlings was planted in the field in the spring of 2015 near Delano, Calif. The new grapevine was selected from this seedling population on Jul. 8, 2017. It was then propagated by cuttings and was bench grafted to 'Freedom' (unpatented) rootstock in 2018. The present invention has been found to retain its distinctive characteristics through two successive asexual propagations.

Grapevine named 'SV35-182-213' differs from its female parent grapevine named 'SV21-66-226' (U.S. Plant Pat. No. 24,531) in that grapevine named 'SV35-182-213' has berries with an elliptic shape as opposed to the ovate shape of grapevine named 'SV21-66-226' (U.S. Plant Pat. No. 24,531). Additionally, grapevine named 'SV35-182-213' ripens in late July whereas grapevine named 'SV21-66-226' (U.S. Plant Pat. No. 24,531) ripens in the second week of August in the Delano, Calif. area.

Grapevine named 'SV35-182-213' differs from its male parent, grapevine named 'SV27-82-371' (unpatented) by having elliptic berries which are crisp while grapevine named 'SV27-82-371' (unpatented) has berries which are spherical and slightly soft in texture.

Grapevine named 'SV35-182-213' is most similar to commercially available commercial cultivar 'Sheegene-21' (U.S. Plant Pat. No. 23,837) but differ from it in that the clusters of grapevine named 'SV35-182-213' are smaller with about 80 berries per cluster while commercial cultivar 'Sheegene-21' (U.S. Plant Pat. No. 23,837) have about 156 berries per cluster. Additionally, grapevine named 'SV35-182-213' ripens in early August while commercial cultivar 'Sheegene-21' (U.S. Plant Pat. No. 23,837) ripens in early July.

SUMMARY OF THE INVENTION

The following are the most outstanding and distinguishing characteristics of this new variety when grown under normal horticultural practices near McFarland, Calif.:

1. Fruit clusters with large, green berries with muscat flavor; and
2. Berries which are very responsive to applications of exogenous gibberellic acid which along with trunk girdling increase the natural berry size by about thirty percent.

BRIEF DESCRIPTION OF THE DRAWINGS

This new grapevine is illustrated by the accompanying photographs which show fruit clusters, leaves, canes and tendrils. The colors shown are as true as can be reasonably obtained by conventional photographic procedures. The photographs were taken from the original seedling vine in 2017. The remainder of the photographs were taken from a vine grafted to 'Freedom' (unpatented) rootstock in 2020 and 2021.

DETAILED BOTANICAL DESCRIPTION

Figure 1:
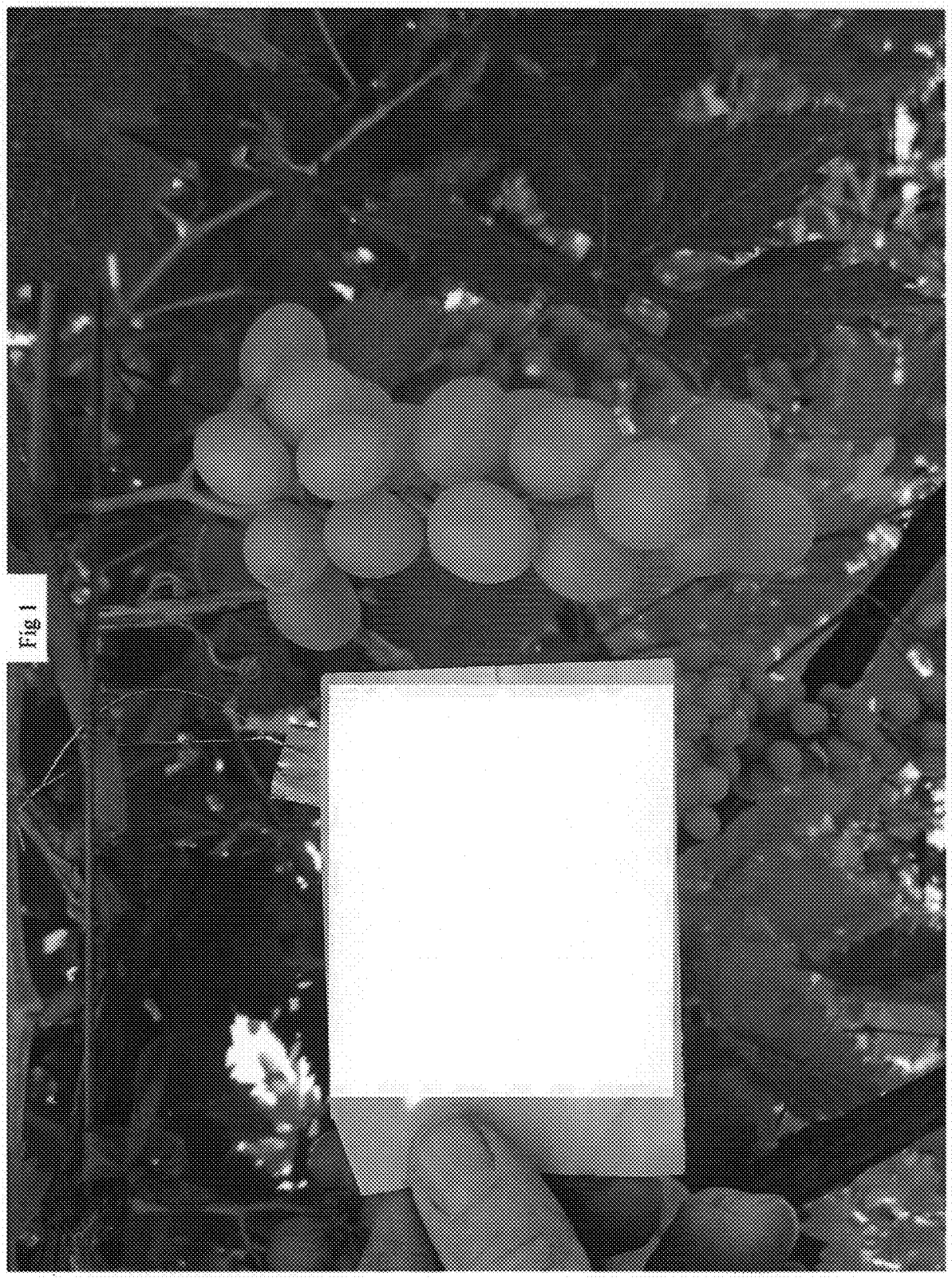
FIG. 1 Fruit cluster on the seedling vine taken in July, 2017.
Figure 2:
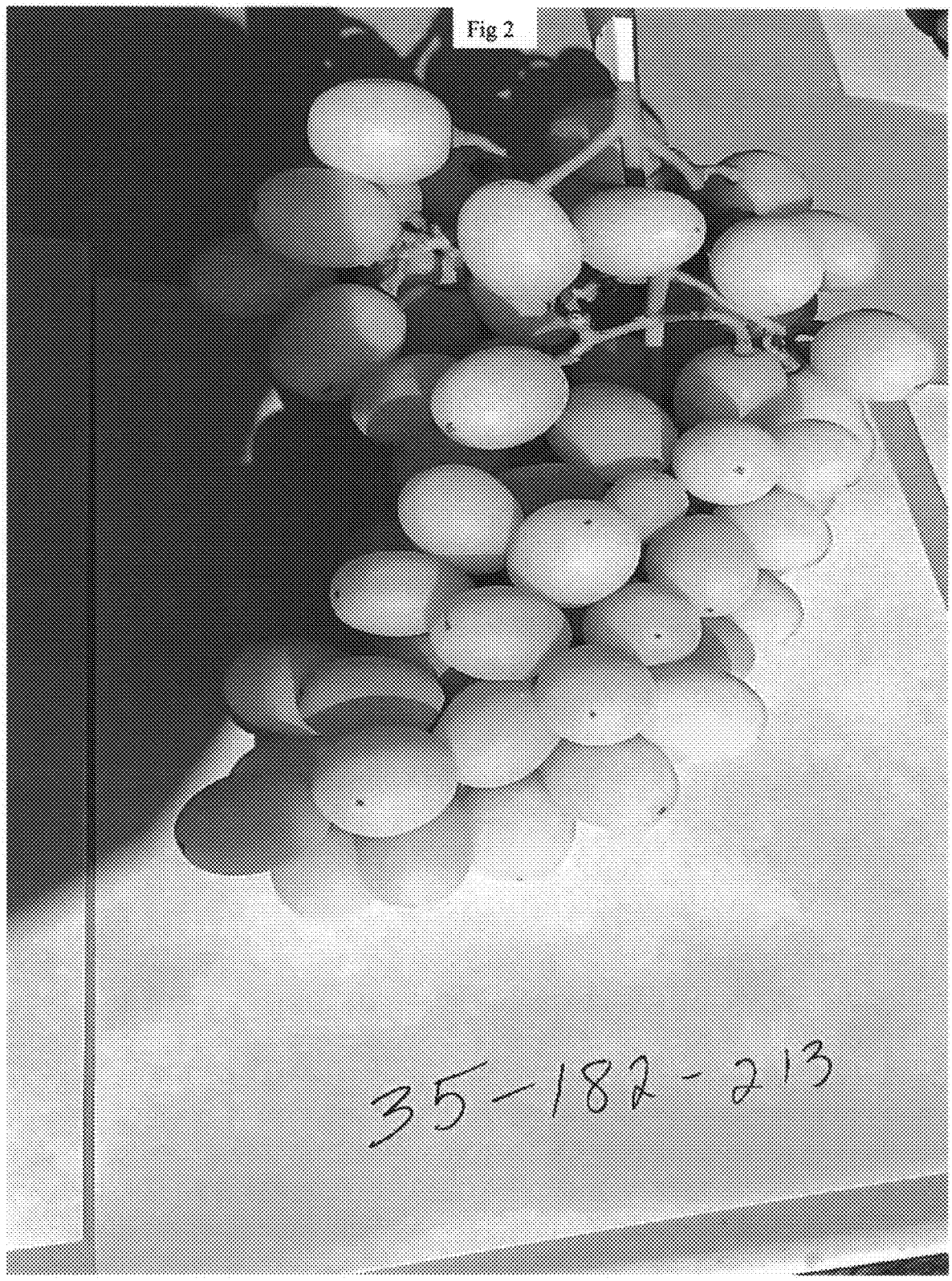
FIG. 2 Fruit cluster from vine which was treated with gibberellic acid and trunk girdling taken in 2021.
Figure 3:
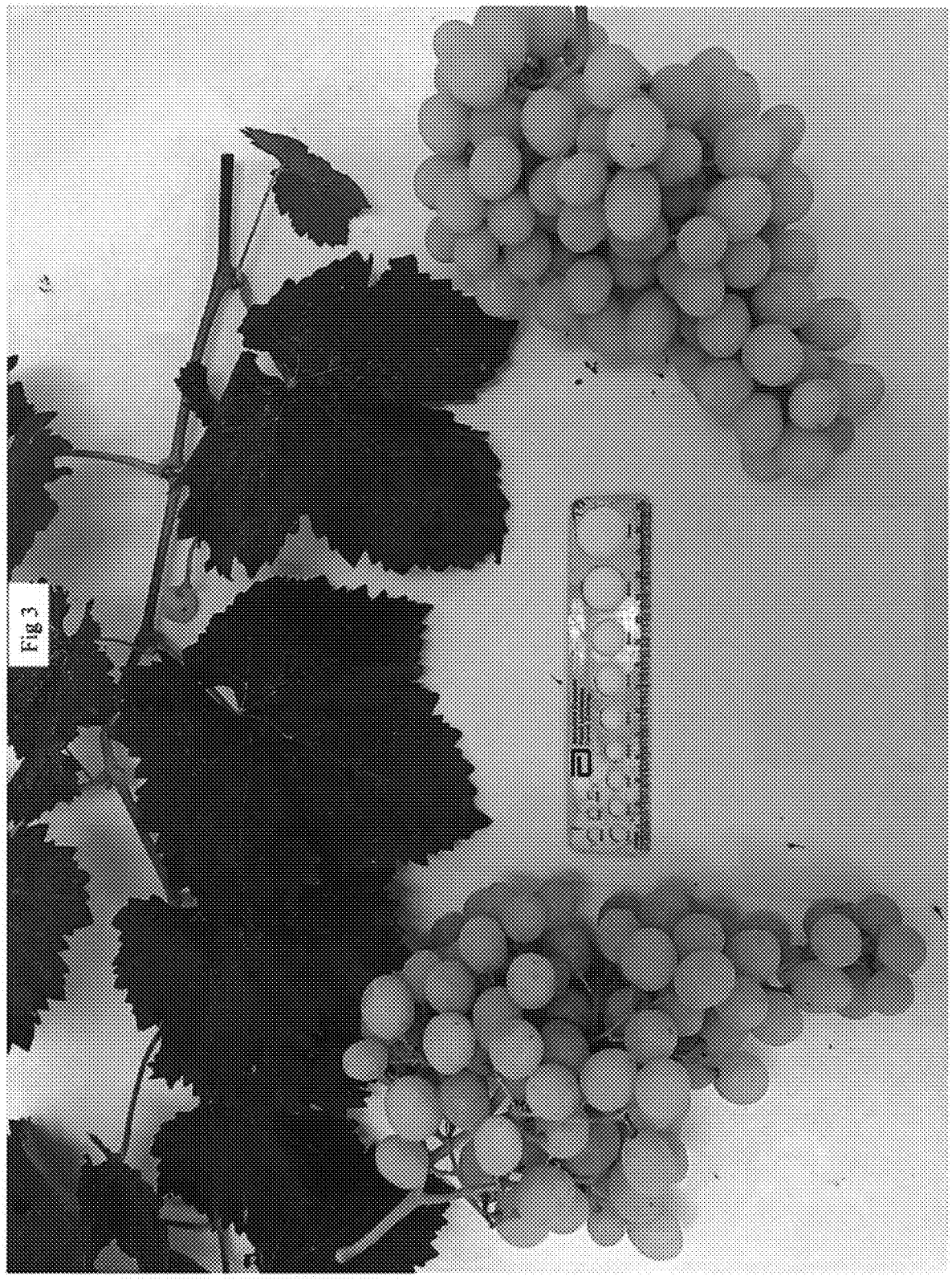
FIG. 3 Cane, leaves, tendrils and shoot tip from vine treated with gibberellic acid and trunk girdling. Natural fruit cluster at left and fruit cluster from vine treated with gibberellic acid and trunk girdling, right, taken in 2021.
Figure 4:
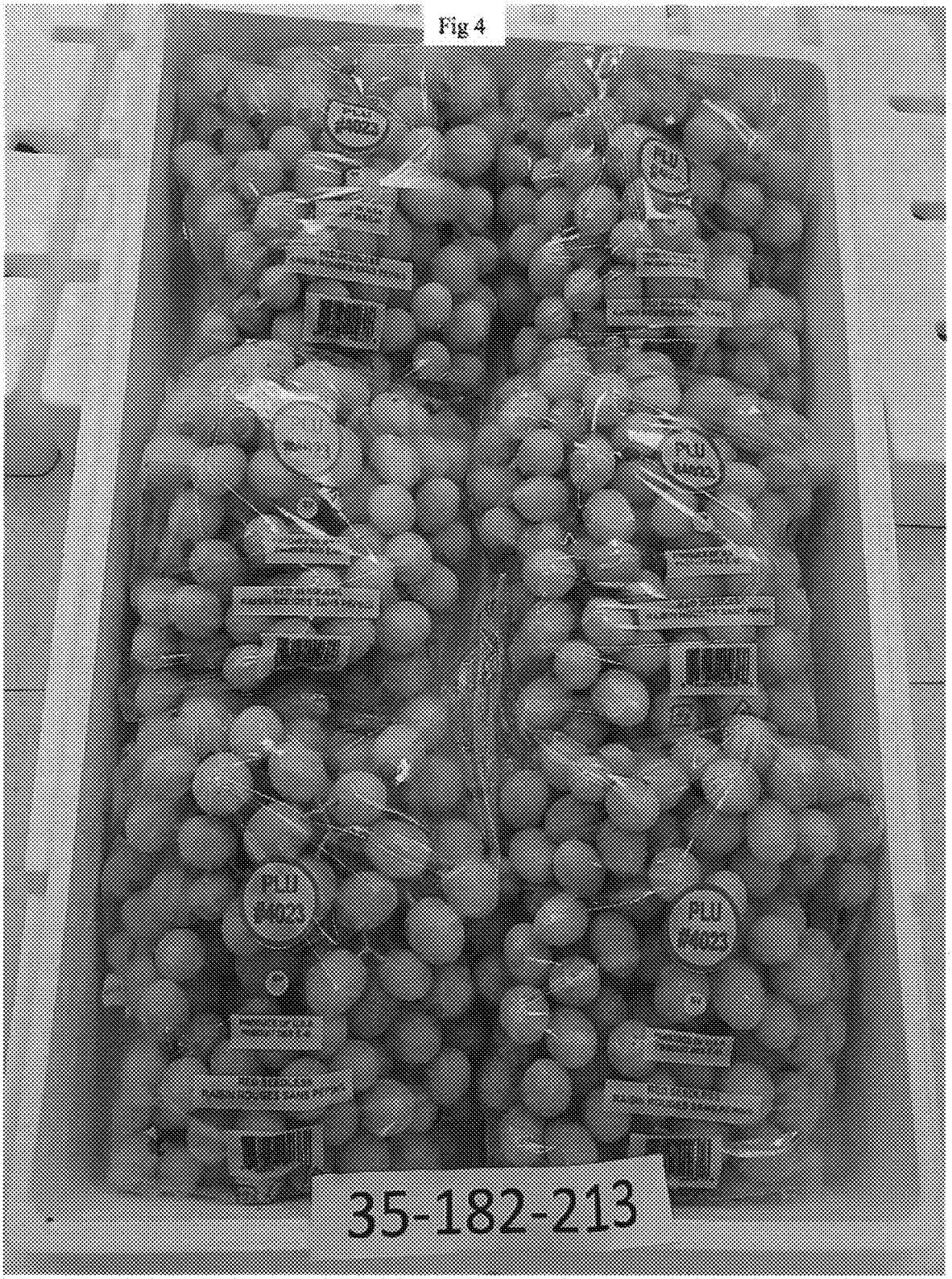
FIG. 4. Box of fruit from vine treated with gibberellic acid and trunk girdling, taken in 2021.

The following detailed description sets forth the distinctive characteristics of grapevine named 'SV35-182-213'. Descriptions of the new invention apply to vines of grapevine named 'SV35-182-213' grown on 'Freedom' (unpatented) rootstock at a density of 1,537 vines per hectare grown near McFarland, Calif. in 2020 and 2021. These vines were observed two years following planting and in the following year, having been planted in 2018. These descriptions are believed to apply generally to the new cultivar grown under similar circumstances elsewhere. Color references are to The Royal Horticultural Society's Colour Chart, The Royal Horticultural Society, London, United Kingdom, 1966, 1986, 1995, 2001. Descriptors used herein conform to those set forth by the International Board for Plant Genetic Resources Institute Grape Descriptors (*Vitis* spp.) of Vigne et du Vin (OIV) and the International Union for the Protection of New Varieties of Plants (UPOV) and published in *Descriptors for Grapevine* (*Vitis spp.*) (Anonymous, International Plant Genetics Resource Institute, 1997, ISBN 92-9043-352-3).

Classification:

*Family*.—Vitaceae.
*Botanical name*.—*Vitis vinifera* L.
*Variety name*.—'SV35-182-213'.

Plant:

*Vigor*.—Moderate, vines spur-pruned and shoot thinned to 32 shoots produce 175 cm of growth per cane.
*Density of foliage*.—Dense.
*Productivity*.—Very productive when spur pruned, up to 28, 625 kg/hectare.
*Hardiness*.—Hardiness observed to 0° C.
*Rootstock*.—'Freedom' (unpatented).
*Bud burst*.—Medium Trunk:

*Shape*.—Broadly elliptical.
*Straps*.—Long, split.
*Surface texture*.—Shaggy.
*Trunk circumference*.—18 cm at 1.0 m of height.
*Inner bark color*.—RHS Greyed Orange group 175A.
*Outer bark color*.—RHS Grey group 201B.

Mature leaves:

*Average blade length*.—15.3 cm.
*Average blade width*.—20.7 cm.
*Size of blade*.—Large.
*Shape*.—Pentagonal.
*Anthocyanin coloration of main veins on the upper side of the blade*.—Absent.
*Mature leaf profile*.—Margins within the plane of blade.
*Blistering* (*upper surface*).—Absent.
*Leaf blade tip*.—In the plane of blade.
*Margins*.—Lobed and serrated.
*Apex*.—Broadly acuminate.
*Bases*.—Sagittate.
*Thickness*.—Medium.
*Undulation of blade between main and lateral veins*.—Slight.
*Shape of teeth*.—Broadly conical, both sides convex.
*Length of teeth*.—About 0.7 mm.
*Width of teeth*.—About 1.0 mm.
*Ratio length/width of teeth*.—About 0.7 to 1.0.
*General shape of petiole sinus*.—Closed.
*Tooth at petiole sinus*.—Absent.
*Petiole sinus limited by veins*.—Absent.
*Shape of upper lateral sinus*.—Open.
*Depth of upper lateral sinus*.—Shallow.
*Prostrate hairs between veins* (*lower surface*).—Very sparse.
*Erect hairs between veins* (*lower surface*).—Absent.
*Prostrate hairs on main veins* (*lower surface*).—Very sparse.
*Density of erect hairs on main veins* (*lower surface*).—Sparse.
*Prostrate hairs on main veins* (*upper surface*).—Very sparse.
*Upper surface*.—Summer color: RHS Yellow Green group 147A. Surface texture: Smooth. Surface appearance: Dull. Goffering of blade: Absent.
*Lower surface*.—Summer color: RHS Green group 137C. Anthocyanin coloration of main veins on lower leaf surface: Absent. Anthocyanin coloration on laterals: Absent. Glossiness: Low. Surface texture: Rough. Surface appearance: Dull.
*Petiole*.—Length: 11.3 cm. Length of petiole compared to middle vein: Considerably shorter. Density of prostrate hairs: Very sparse. Density of erect hairs: Dense. Color: In shade: RHS Yellow Green group 145A. In sun: RHS Yellow Green group 144C.

Tendrils:

*Number*.—Bifurcated and trifurcated; forming irregularly above node 7.
*Length*.—8.0 cm.
*Diameter*.—2 mm.
*Texture*.—Smooth.
*Color*.—RHS Yellow Green group 144B.

Growing tips:

*Color*.—RHS Yellow green group 144B.
*Anthocyanins*.—Absent.

*Shape*.—Flattened.
*Apex*.—Fully open.
*Prostrate hair on tips*.—Sparse.
*Anthocyanin coloration of prostrate hairs on tips*.—Absent.
*Erect hairs on tip*.—Absent.

Young shoots:
*Shoot attitude*.—Erect.
*Color of dorsal side of internode*.—RHS Yellow Green group 144B.
*Color of ventral side of internode*.—RHS Yellow Green group 144C.
*Color of dorsal side of nodes*.—RHS Yellow Green group 145A.
*Color of ventral side of nodes*.—RHS Yellow Green group 145A.
*Erect hairs on internodes*.—Absent.

Woody shoot:
*Canes*.—Shape: Broadly elliptical. Internode length: About 9.7 cm. Width at node: 10.2 mm. Cross section: Circular. Surface: Smooth. Main color: RHS Greyed orange group 175B. Lenticels: Inconspicuous.
*Buds*.—Shape: Pointed. Cane bud fruitfulness: Basal buds fruitful, usually 2 clusters per shoot. Length: 3.2 mm. Width: 3.0 mm. Height: 3.4 mm. Color: RHS Greyed Orange group 176A.

Flowers:
*Flower sex*.—Perfect.
*Pollen color*.—RHS Yellow group 9C.
*Pollen amount*.—Abundant.
*Position of first flowering nodes*.—4th node.
*Number of inflorescences per shoot*.—1 or 2.
*Calyptra color*.—RHS Yellow green group 144A.
*Ovary length*.—3 mm.
*Ovary width*.—1 mm.
*Ovary color*.—RHS Green group 143A.
*Filament length*.—3 mm.
*Filament color*.—Translucent white, absence of pigmentation.
*Anther length*.—1 mm.
*Anther color*.—RHS Yellow group 9C.
*Date of full bloom*.—May 6, 2021.

Fruit:
*Ripening period*.—Early mid-season at McFarland, Calif.
*Date of ripening*.—Aug. 3, 2021 at McFarland, Calif.
*Use*.—Fresh market.
*Keeping quality*.—Very good.
*Shipping quality*.—Good.
*Solids-sugar*.—High, about 20.5 brix at full maturity.
*Titratable acidity*.—0.42 g/liter
*Ph of juice*.—3.96.
*Dimensions* (*natural*).—Longitudinal axis about 2.5 cm at base, horizontal axis: about 2.3 cm.
*Dimensions* (*with gibberellic acid treatment*).—Longitudinal axis: About 2.9 about base; horizontal axis: about 2.4 cm.
*Bunch*.—Size: Medium. Length (peduncle excluded): About 16.9 cm. Width: About 13.5 cm. Weight: Natural, without gibberellic acid treatment: 522 g. With gibberellic acid treatment: 582.5 g. Density: Well-filled, but loose. Number of berries: 80.7. Form: Conical.
*Peduncle*.—Length: About 5.0 cm. Lignification: Medium. Color: RHS Yellow Green group 146C.
*Berry*.—Size: Large. Uniformity of size: Uniform. Weight Natural, without gibberellic acid treatment: 6.5 g. With gibberellic acid treatment: 8.3 g. Shape: Natural, without gibberellic acid treatment: Elliptic. With gibberellic acid treatment: Elliptic. Presence of seeds: Seedless; most berries develop one or two small, soft rudimentary seeds about 5 mm in length. Cross section: Circular. Dimensions: Longitudinal axis: About 2.5 cm at base. Horizontal axis: About 2.3 cm. Skin color (without bloom): RHS Yellow Green group 151A. Coloration of flesh: Yellow Green group 150C. Juiciness of flesh: Very juicy. Berry firmness: Very firm. Particular flavor: Muscat. Bloom (cuticular wax): Strong. Pedicel length: 9.8 mm. Berry separation from pedicel: With difficulty.
*Skin*.—Thickness: Medium. Texture: Crisp. Reticulation: Absent. Roughness: Absent. Tenacity: Tenacious to flesh. Tendency to crack: Resistant.

Disease and insect resistance: No particular resistance or susceptibility has been observed. Normal disease control practices can be used.

Having thus described and illustrated our new variety of grapevine, we claim:

1. A new and distinct variety of grapevine plant named 'SV35-182-213', substantially as illustrated and described herein.

* * * * *